(12) United States Patent
Mertens et al.

(10) Patent No.: US 7,807,122 B2
(45) Date of Patent: Oct. 5, 2010

(54) METALLOALUMINOPHOSPHATE MOLECULAR SIEVES, THEIR SYNTHESIS AND USE

(75) Inventors: Machteld Maria Mertens, Boortmeerbeek (BE); Karl G. Strohmaier, Port Murray, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1013 days.

(21) Appl. No.: 11/588,669

(22) Filed: Oct. 27, 2006

(65) Prior Publication Data
US 2007/0100188 A1 May 3, 2007

Related U.S. Application Data

(60) Provisional application No. 60/732,830, filed on Nov. 2, 2005.

(51) Int. Cl.
| | |
|---|---|
| C01B 39/54 | (2006.01) |
| C01B 39/04 | (2006.01) |
| C01B 39/46 | (2006.01) |
| C01B 39/48 | (2006.01) |
| C01B 37/08 | (2006.01) |
| C07C 209/16 | (2006.01) |
| C07C 1/20 | (2006.01) |
| C07C 1/24 | (2006.01) |

(52) U.S. Cl. ................ 423/306; 423/702; 423/704; 423/705; 423/706; 423/707; 423/708; 423/DIG. 30

(58) Field of Classification Search ............ 423/306, 423/702, 704, 705, 706, 707, 718, DIG. 30; 585/638, 640; 564/464, 479
See application file for complete search history.

(56) References Cited

U.S. PATENT DOCUMENTS

| | | | |
|---|---|---|---|
| 4,440,871 A | 4/1984 | Lok et al. | |
| 4,567,029 A | 1/1986 | Wilson et al. | |
| 5,279,810 A | 1/1994 | Calabro | |
| 5,912,393 A | 6/1999 | Barger et al. | |
| 6,334,994 B1 | 1/2002 | Wendelbo et al. | |
| 6,812,372 B2 | 11/2004 | Janssen et al. | |
| 6,903,240 B2* | 6/2005 | Mertens et al. | 585/639 |
| 6,953,767 B2 | 10/2005 | Janssen et al. | |
| 7,459,136 B2* | 12/2008 | Mertens | 423/306 |
| 7,528,201 B2* | 5/2009 | Mertens et al. | 526/75 |
| 7,622,624 B2* | 11/2009 | Mertens et al. | 585/640 |
| 2004/0215044 A1 | 10/2004 | Mertens et al. | |
| 2005/0096214 A1 | 5/2005 | Janssen et al. | |

FOREIGN PATENT DOCUMENTS

EP   1 142 833   10/2001

OTHER PUBLICATIONS

Ashtekar et al, "Small Pore Aluminum Phosphate Molecular Sieves with Chabazite Structure: . . . " J. Phys. Chem. (1996), 100, 3665-3670.*
Lok et al, "Silicoaluminophosphate Molecular Sieves: . . . ", J. Am. Chem. Soc., (1984), 106, 6092-6093.*
Jiesheng Chen et al., "SAPO-18 Catalysts and Their Bronsted Acid Sites," J. Phys. Chem., American Chemical Society, vol. 98, pp. 10216-10224, 1994.
Jiesheng Chen et al., "Silicoaluminophosphate No. eighteen (SAPO-18): a new microporous solid acid catalyst," Catalysis Letters, vol. 28, pp. 241-248, 1994.
Yan Xu et al., "The Synthesis of SAPO-34 and CoSAPO-34 from a Triethylamine-Hydrofluoric Acid-Water System," J. Chem. Soc., Faraday Trans., pp. 425-429, vol. 86(2), 1990.
A.M. Prakesh et al., "Synthesis of SAPO-34: High Silicon Incorporation in the Presence of Morpholine as Template," J. Chem. Soc., Faraday Trans., vol. 90(15), pp. 2291-2296, 1994.
J. Chen et al., "Understanding the Bronsted Acidity of SAPO-5, SAPO-17, SAPO-18 and SAPO-34 and their Catalytic Performance for Methanol Conversion to Hydrocarbons," Zeolites and Related Microporous Materials: State of the Art 1994; Studies in Surface Science and Catalysis, vol. 84, pp. 1731-1738.

* cited by examiner

*Primary Examiner*—David M Brunsman
(74) *Attorney, Agent, or Firm*—David M. Weisberg

(57) ABSTRACT

A process for manufacturing a metalloaluminophosphate molecular sieve, the process comprising the steps of: (a) combining at least one silicon source, at least one metal source, at least one structure-directing-agent (R), at least one phosphorus source, and at least one aluminum source to form a mixture having a molar composition according to formula:

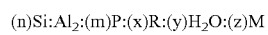

(n)Si:Al$_2$:(m)P:(x)R:(y)H$_2$O:(z)M wherein n is in the range of from about 0.005 to about 0.6, m is in the range of from about 1.2 to about 2.4, x is in the range of from about 0.5 to about 2, y is in the range of from about 10 to about 60, and z is in the range of from about 0.001 to 1; and (b) submitting the mixture to crystallization conditions to form the metalloaluminophosphate molecular sieve, wherein the metalloaluminophosphate molecular sieve has an X-ray diffraction pattern having a FWHM greater than 0.10 degree (2θ) and an AEI/CHA framework type ratio of from about 0/100 to about 40/60 as determined by DIFFaX analysis.

59 Claims, 6 Drawing Sheets

METALLOALUMINOPHOSPHATE MOLECULAR SIEVES, THEIR SYNTHESIS AND USE

CROSS-REFERENCE TO RELATED APPLICATIONS

This application claims priority to Provisional application filed on Nov. 2, 2005, U.S. Ser. No. 60/732,830.

FIELD OF THE INVENTION

This invention relates to a process for manufacturing metalloaluminophosphate molecular sieves, a metalloaluminophosphate molecular sieve composition, and their use in a process for making an olefin product by contacting these metalloaluminophosphate molecular sieves with an oxygenate feedstock.

BACKGROUND OF THE INVENTION

Metalloaluminophosphate (MeAPO) molecular sieves contain lattice metal in tetrahedral coordination with oxygen atoms in a three-dimensional microporous crystal framework structure of $[SiO_2]$, $[AlO_2]$, and $[PO_2]$ corner sharing tetrahedral units. The $[PO_2]$ tetrahedral units are provided by a variety of compositions including phosphoric acid, organic phosphates such as triethyl phosphate, and aluminophosphates. The $[AlO_2]$ tetrahedral units are provided by a variety of compositions including aluminum alkoxides such as aluminum isopropoxide, aluminum phosphates, aluminum hydroxide, sodium aluminate, and pseudoboehmite. The $[SiO_2]$ tetrahedral units are provided by a variety of compositions including silica sols and silicon alkoxides such as tetraethylorthosilicate and fumed silica. The metal tetrahedral units are provided by a variety of compositions including Mg, Mn, Zn, and Co compounds.

SAPO-34 and SAPO-18 have been reported as suitable catalysts for light olefin production from methanol. SAPO-34 belongs to the family of molecular sieves having the structure type of the zeolitic mineral chabazite (CHA). The preparation and characterization of SAPO-34 has been reported in several publications, including U.S. Pat. No. 4,440,871; J. Chen et al. in "Studies in Surface Science and Catalysis", Vol. 84, pp. 1731-1738; U.S. Pat. No. 5,279,810; J. Chen et al. in "Journal of Physical Chemistry", Vol. 98, pp. 10216-10224, 1994; J. Chen et al. in "Catalysis Letters", Vol. 28, pp. 241-248, 1994; A. M. Prakash et al. in "Journal of the Chemical Society, Faraday Transactions," Vol. 90(15), pp. 2291-2296, 1994; Yan Xu et al. in "Journal of the Chemical Society, Faraday Transactions" vol. 86(2), pp. 425-429, 1990, all of which are herein fully incorporated by reference.

U.S. Pat. No. 6,334,994, incorporated herein by reference, discloses a silicoaluminophosphate molecular sieve, referred to as RUW-19, which is said to be an AEI/CHA mixed phase composition. In particular, RUW-19 is reported as having peaks characteristic of both CHA and AEI framework type molecular sieves, except that the broad feature centered at about 16.9 (2θ) in RUW-19 replaces the pair of reflections centered at about 17.0 (2θ) in AEI materials and RUW-19 does not have the reflections associated with CHA materials centered at 2θ values of 17.8 and 24.8. DIFFaX analysis of the X-ray diffraction pattern of RUW-19 as produced in Examples 1, 2, and 3 of U.S. Pat. No. 6,334,994 indicates that these materials are characterized by single intergrown phases of AEI and CHA framework type molecular sieves with AEI/CHA ratios of about 60/40, 65/35, and 70/30, respectively.

Throughout this description, the XRD reflection values are referred to as (2θ), which is synonymous to the expression "degrees 2θ."

U.S. Pat. No. 6,812,372, incorporated herein by reference, discloses a silicoaluminophosphate molecular sieve, comprising at least one intergrown phase of molecular sieves having AEI and CHA framework types, wherein said intergrown phase has an AEI/CHA ratio of from about 5/95 to 40/60 as determined by DIFFaX analysis, using the powder X-ray diffraction pattern of a calcined sample of said metalloaluminophosphate molecular sieve.

U.S. patent application Ser. Nos. 10/092,792 and 10/995,870 disclose a silicoaluminophosphate molecular sieve comprising at least one intergrown phase of molecular sieves having AEI and CHA framework types, wherein the intergrown phase has an AEI/CHA ratio of from about 5/95 to 40/60 as determined by DIFFaX analysis, using the powder X-ray diffraction pattern of a calcined sample of the metalloaluminophosphate molecular sieve. It also relates to methods for its preparation and to its use in the catalytic conversion of methanol to olefins.

U.S. patent application Ser. No. 10/425,587 discloses methods and compositions of synthesis mixtures for the synthesis of aluminophosphates and silicoaluminophosphate molecular sieves, which enable the control and adjustment of the crystal particle size of aluminophosphates and silicoaluminophosphate molecular sieves. The synthesis mixture compositions used have two or more organic templates present at a molar ratio of total template to aluminum of $\leq 1.25$; such a synthesis mixture is susceptible to control of product particle size through variation in the amount of seeds used in the synthesis.

U.S. Pat. No. 4,567,029 discloses a crystalline microporous metal aluminophosphate compositions containing as lattice constituents in addition to $AlO_2$ and $PO_2$ structure units, one or a mixture of two or more of the metals Mg, Mn, Co, and Zn in tetrahedral coordination with oxygen atoms (MAPO).

U.S. Pat. No. 5,912,393 discloses a catalyst for converting methanol to light olefins. The catalyst is a metalloaluminophosphate molecular sieve having the empirical formula $(EL_xAl_yP_z)O_2$ where EL is a metal such as silicon or magnesium and x, y, and z are the mole fractions of EL, Al, and P respectively. The molecular sieve has a crystal morphology in which the average smallest crystal dimension is at least 0.1 microns. Use of this catalyst gives a product with a larger amount of ethylene versus propylene.

EP Patent Application No. 1,142,833 discloses a class of microporous metalloaluminophosphate molecular sieves (MeAPSOs) and the method of their fast preparation. These molecular sieves can be represented by the empirical formula on an anhydrous basis: $mR.(M_qSi_xAl_yP_z)O_2$, wherein "R" represents the templating agent presented in the intracrystalline pore system; "m" is the molar amount of "R" per mole of $(M_qSi_xAl_yP_z)O_2$ and has a value from 0.01 to 8.00; "M" represents at least one metal element; "q", "x", "y", and "z" represent the molar fractions of metal, silicon, aluminum, and phosphorus respectively, whose variations are q=0–0.98, x=0–0.98, y=0.01–0.60, z=0.01–0.60, and q+x+y+z=1. The crystallization time of the synthesis is 0.5-12 hours, which is defined as the method of fast preparation.

SUMMARY OF THE INVENTION

The present invention is related to a metalloaluminophosphate molecular sieve having an X-ray diffraction pattern having a FWHM greater than 0.10 degree (2θ) and an AEI/CHA framework type ratio of from about 0/100 to about 40/60 as determined by DIFFaX analysis and a process for manufacturing and using such metalloaluminophosphate molecular sieves.

In one embodiment, the present invention relates to a process for manufacturing a metalloaluminophosphate molecular sieve, the process comprising the steps of:

(a) combining at least one silicon source, at least one metal source, at least one structure-directing-agent (R), at least one phosphorus source, and at least one aluminum source to form a mixture having a molar composition according to formula (I):

(n)Si:Al$_2$:(m)P:(x)R:(y)H$_2$O:(z)M     (I)

wherein n is in the range of from about 0.005 to about 0.6, m is in the range of from about 1.2 to about 2.4, x is in the range of from about 0.5 to about 2, y is in the range of from about 10 to about 60, and z is in the range of from about 0.001 to 1; and (b) submitting the mixture to crystallization conditions to form the metalloaluminophosphate molecular sieve, wherein the metalloaluminophosphate molecular sieve has an X-ray diffraction pattern having a FWHM greater than 0.10 degree (2θ) and an AEI/CHA framework type ratio of from about 0/100 to about 40/60 as determined by DIFFaX analysis.

In another embodiment, this invention relates to a metalloaluminophosphate molecular sieve manufactured in according to the process described in the paragraph above.

In yet another embodiment, this invention relates to a process for the conversion of an oxygenate to olefins, the process comprising the steps of:

(i) contacting the oxygenate under catalytic conversion conditions with the metalloaluminophosphate molecular sieve made in according to the process described above in steps (a) and (b); and (ii) withdrawing the olefins from the reactor.

In yet another embodiment, this invention relates to a metalloaluminophosphate molecular sieve, the metalloaluminophosphate molecular sieve having a composition represented by empirical formula (II) on an anhydrous basis as:

pR●(M$_q$Si$_r$Al$_s$P$_t$)O$_2$     (II)

wherein p is in the range of from about 0.001 to about 0.5, q is in the range of from about 0.001 to about 0.25, r is in the range of from about 0.01 to about 0.15, s is in the range of from about 0.01 to about 0.6, t is in the range of from about 0.001 to 0.6, and the sum of q, r, s, and t is 1, wherein the metalloaluminophosphate molecular sieve has an X-ray diffraction pattern having a FWHM greater than 0.10 degree (2θ) and an AEI/CHA framework type ratio of from about 0/100 to about 40/60 as determined by DIFFaX analysis.

In yet another embodiment, this invention relates to a process for the conversion of an oxygenate to olefins, the process comprising the steps of:

(i) contacting the oxygenate under catalytic conversion conditions with the metalloaluminophosphate molecular sieve having a composition represented by the empirical formula as described above; and (ii) withdrawing the olefins from the reactor.

For each of these embodiments, the metalloaluminophosphate molecular sieve has a shredded crystal morphology by SEM.

DETAILED DESCRIPTION OF THE INVENTION

Figure 1:
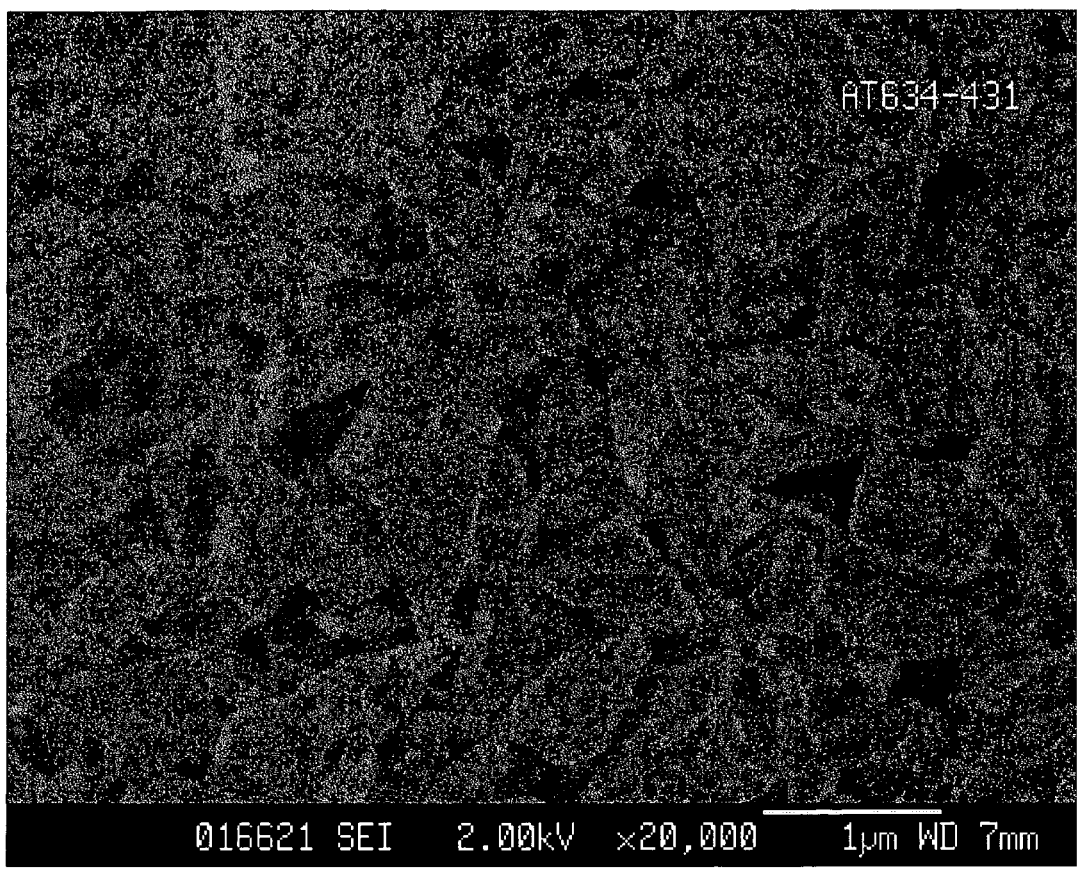
FIG. 1 is a SEM image of a shredded morphology metalloaluminophosphate molecular sieve of Example 4.
Figure 2:
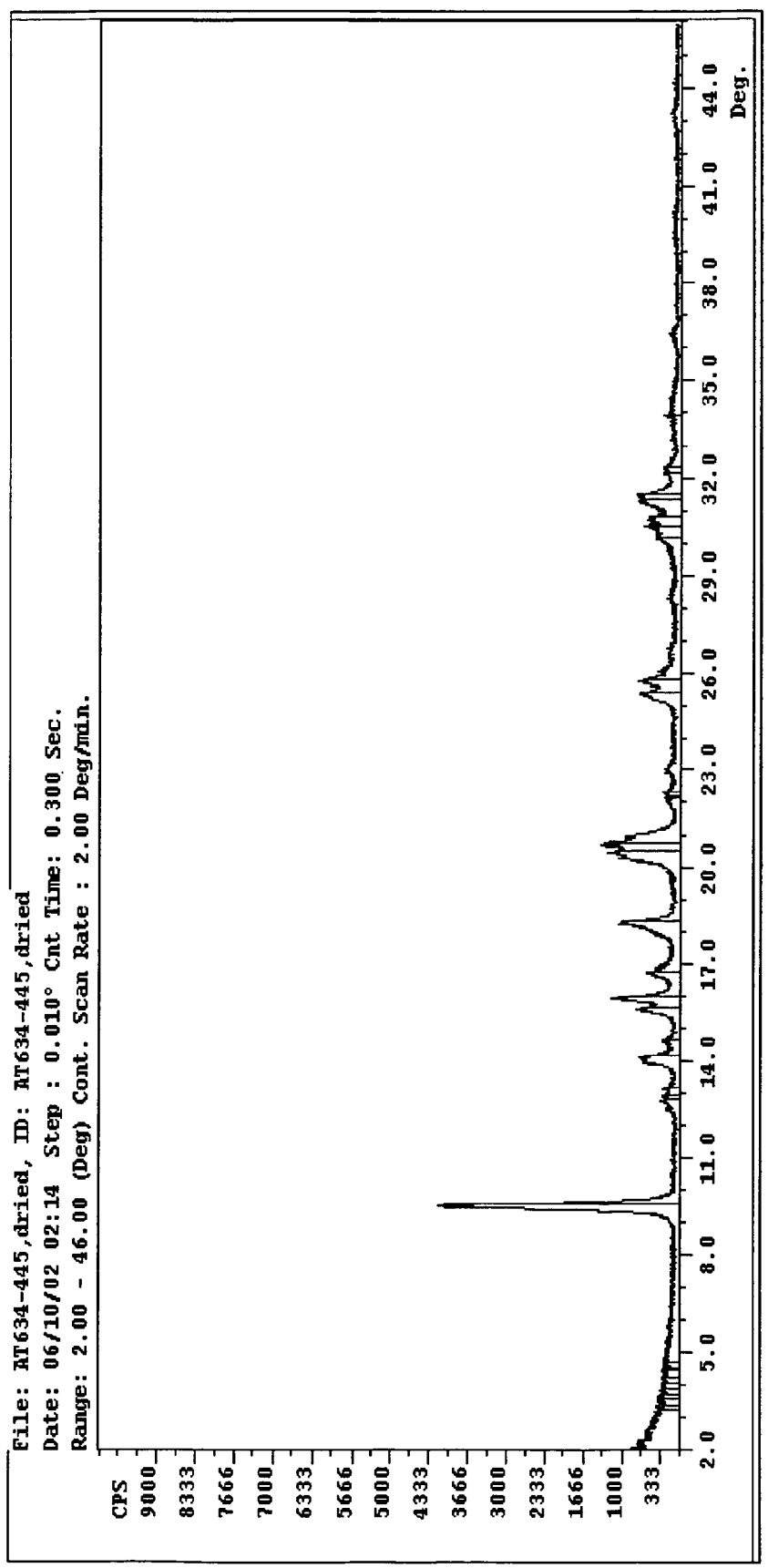
FIG. 2 is an XRD pattern of the metalloaluminophosphate molecular sieve of Example 1.
Figure 3:
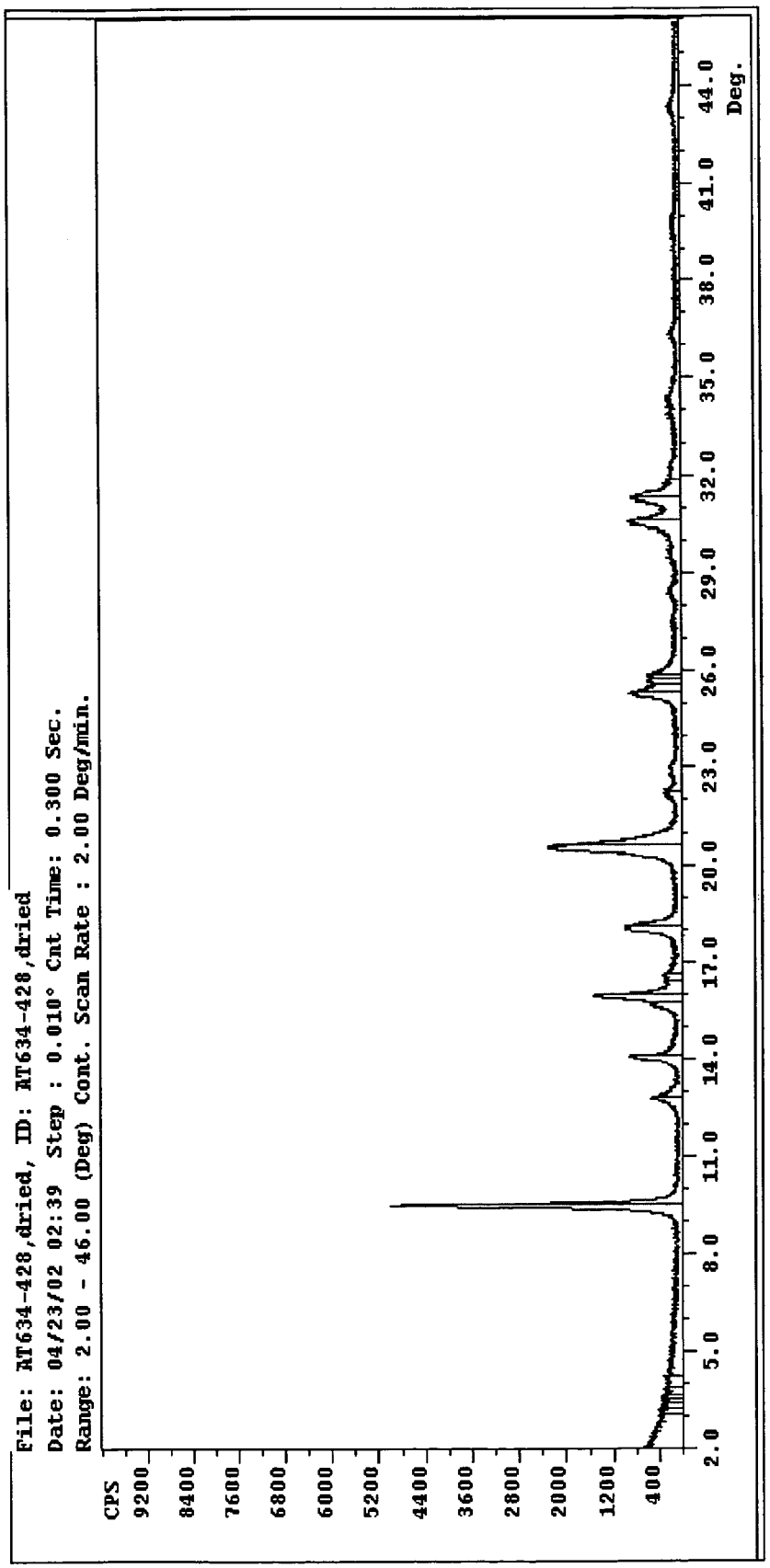
FIG. 3 is an XRD pattern of the metalloaluminophosphate molecular sieve of Example 2.
Figure 4:
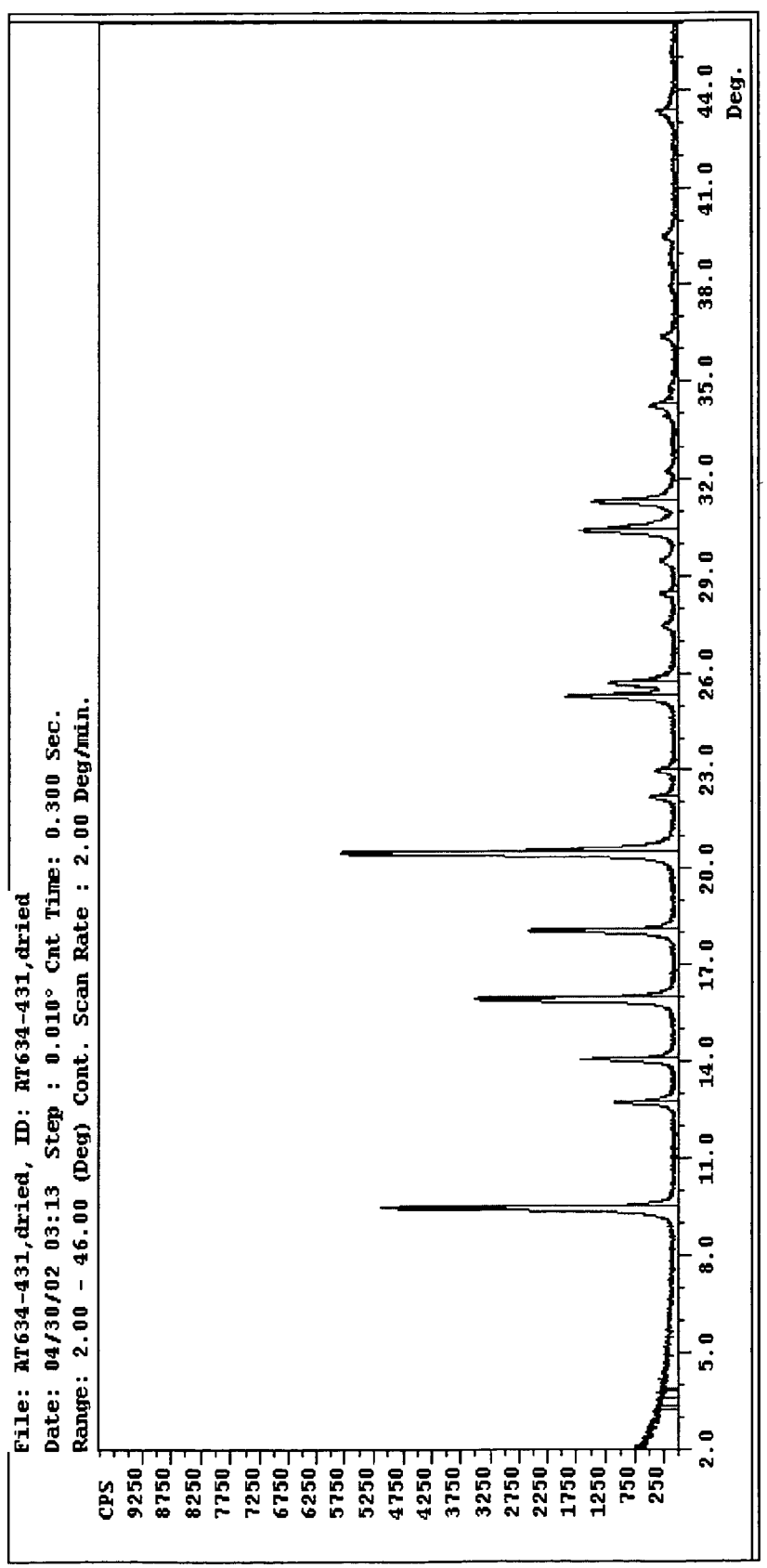
FIG. 4 is an XRD pattern of the metalloaluminophosphate molecular sieve of Example 3.
Figure 5:
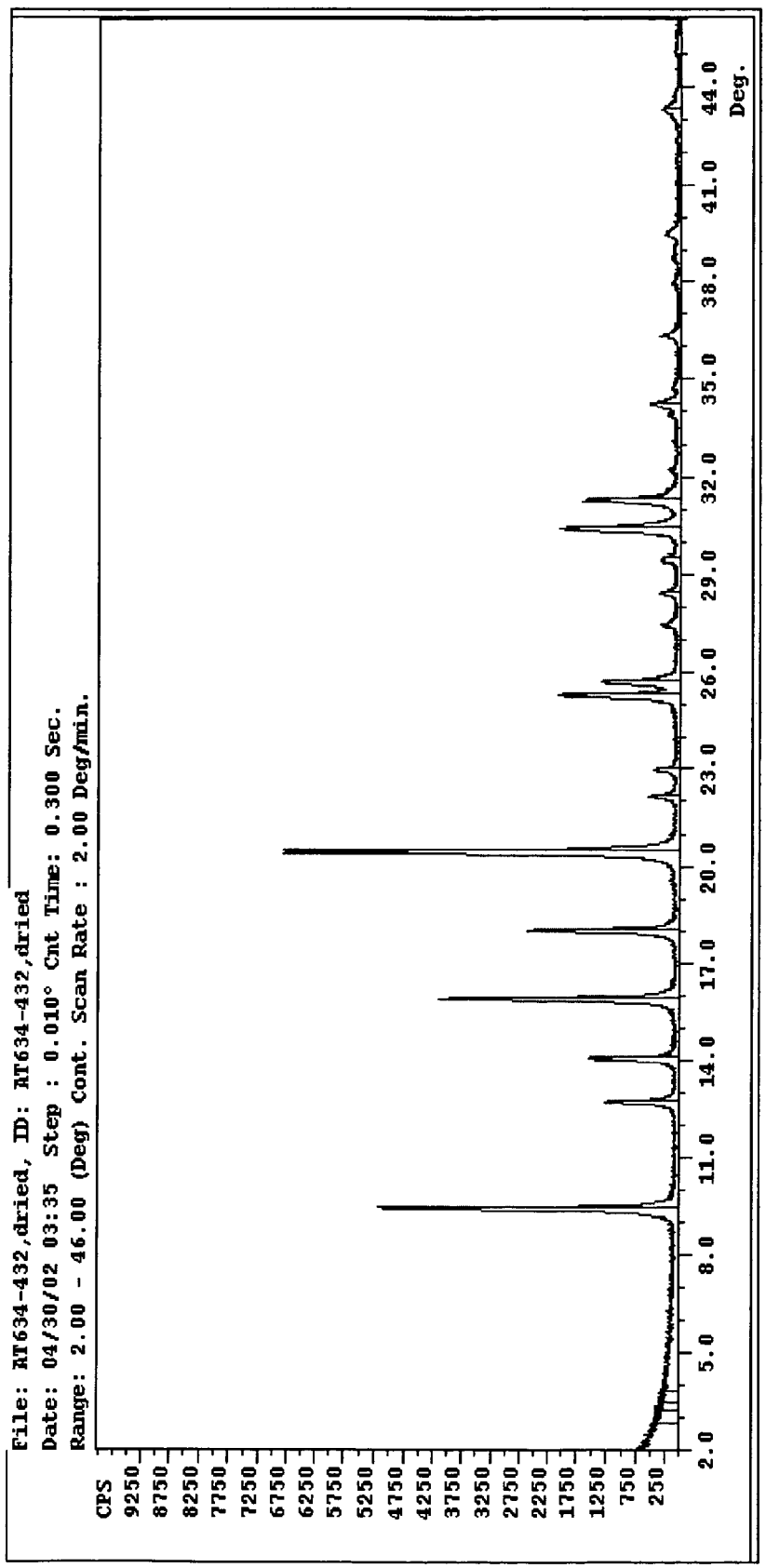
FIG. 5 is an XRD pattern of the metalloaluminophosphate molecular sieve of Example 4.
Figure 6:
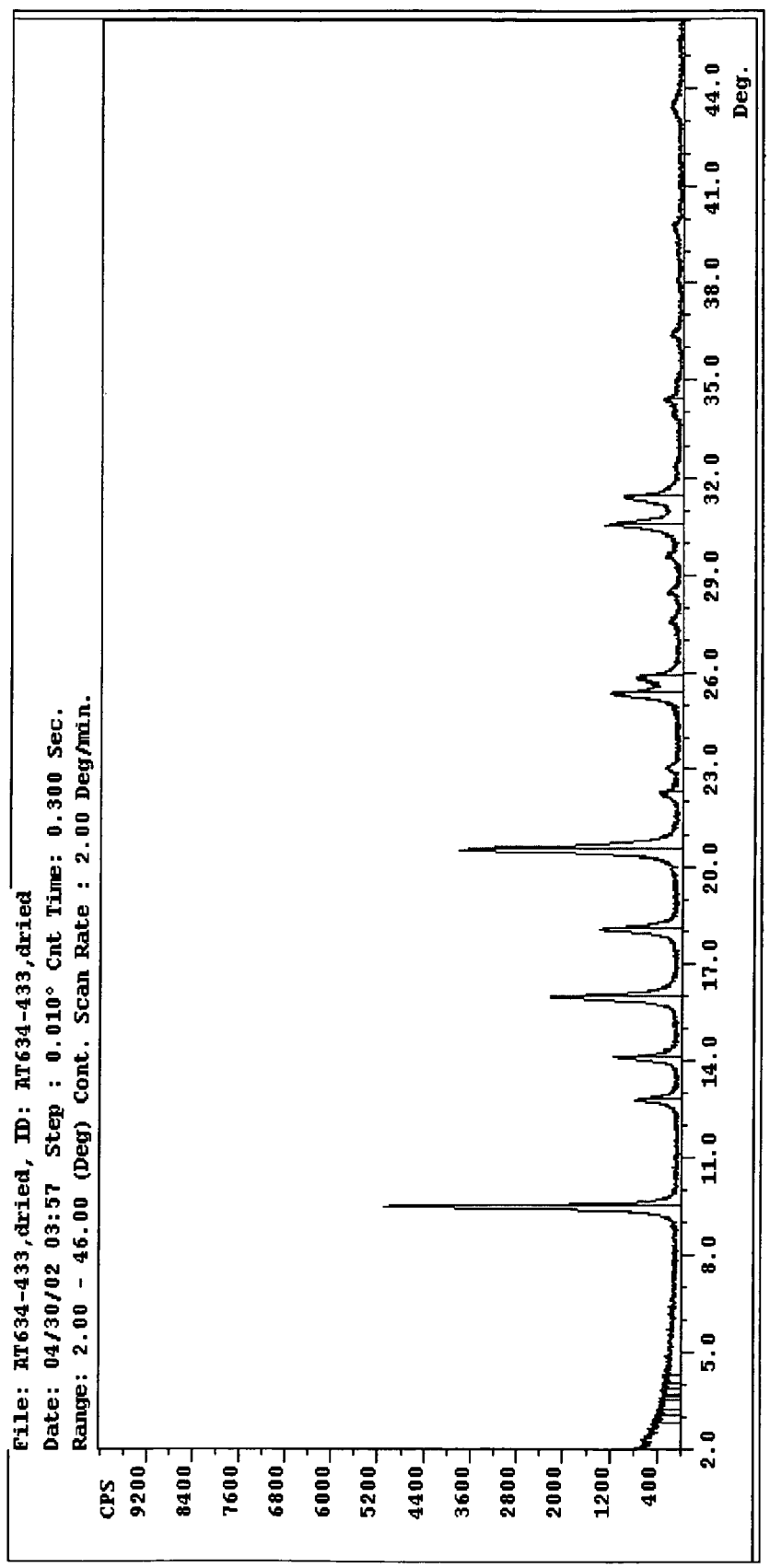
FIG. 6 is an XRD pattern of the metalloaluminophosphate molecular sieve of Example 5.

Metalloaluminophosphate molecular sieves are generally well known to those skilled in the art, for example, U.S. Pat. No. 4,567,029 (MeAPO where Me is Mg, Mn, Zn, or Co), U.S. Pat. No. 4,440,871 (SAPO), EP Application No. E.P. 0,159,624 (ELAPSO where El is As, Be, B, Cr, Co, Ga, Ge, Fe, Li, Mg, Mn, Ti, or Zn), U.S. Pat. No. 4,554,143 (FeAPO); U.S. Pat. Nos. 4,822,478; 4,683,217; 4,744,885 (FeAPSO); EP 0,158,975; and U.S. Pat. No. 4,935,216 (ZnAPSO); EP-A-0 161 489 (CoAPSO); EP 0,158,976 (ELAPO, where EL is Co, Fe, Mg, Mn, Ti, or Zn); U.S. Pat. No. 4,310,440 (AlPO4); Patent Application No. EP 0,158,350 (SENAPSO); U.S. Pat. No. 4,973,460 (LiAPSO); U.S. Pat. No. 4,789,535 (LiAPO); U.S. Pat. No. 4,992,250 (GeAPSO); U.S. Pat. No. 4,888,167 (GeAPO); U.S. Pat. No. 5,057,295 (BAPSO); U.S. Pat. No. 4,738,837 (CrAPSO); U.S. Pat. Nos. 4,759,919, and 4,851,106 (CrAPO); U.S. Pat. Nos. 4,758,419; 4,882,038; 5,434,326; and 5,478,787 (MgAPSO); U.S. Pat. No. 4,554,143 (FeAPO); U.S. Pat. No. 4,894,213 (AsAPSO); U.S. Pat. No. 4,913,888 (AsAPO); U.S. Pat. Nos. 4,686,092; 4,846,956; and 4,793,833 (MnAPSO); U.S. Pat. Nos. 5,345,011 and 6,156,931 (MnAPO); U.S. Pat. No. 4,737,353 (BeAPSO); U.S. Pat. No. 4,940,570 (BeAPO); U.S. Pat. Nos. 4,801,309; 4,684,617; and 4,880,520 (TiAPSO); U.S. Pat. Nos. 4,500,651; 4,551,236; and 4,605,492 (TiAPO); U.S. Pat. Nos. 4,824,554; 4,744,970 (CoAPSO); U.S. Pat. No. 4,735,806 (GaAPSO); Patent Application No. EP 0,293,937 (QAPSO, where Q is framework oxide unit [QO$_2$]); as well as U.S. Pat. Nos. 4,567,029; 4,686,093; 4,781,814; 4,793,984; 4,801,364; 4,853,197; 4,917,876; 4,952,384; 4,956,164; 4,956,165; 4,973,785; 5,241,093; 5,493,066; and 5,675,050; all of which are herein fully incorporated by reference.

Other metalloaluminophosphate molecular sieves include those described in patent No. EP 0,888,187 (microporous crystalline metalloaluminophosphates (UIO-6)), U.S. Pat. No. 6,004,898 (molecular sieve and an alkaline earth metal), U.S. patent application Ser. No. 09/511,943, filed Feb. 24, 2000 (integrated hydrocarbon co-catalyst), PCT WO 01/64340 published Sep. 7, 2001 (thorium containing molecular sieve), and R. Szostak, Handbook of Molecular Sieves, Van Nostrand Reinhold, New York, N.Y. (1992), which are all herein fully incorporated by reference.

The preferred molecular sieves are SAPO molecular sieves and metal substituted SAPO molecular sieves. In one embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium, and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn, and Zr, and mixtures thereof. In a more preferred embodiment, the metal comprises at least one of Mg, Zn, and mixtures thereof.

In one embodiment, the metalloaluminophosphate molecular sieve has a composition represented by empirical formula (II) on an anhydrous basis as:

$$pR\bullet(M_q Si_r Al_s P_t)O_2 \quad (II)$$

wherein R represents at least one templating agent, preferably an organic templating agent; p is the number of moles of R per mole of $(M_q Si_r Al_s P_t)O_2$ and p has a value from about 0.001 to about 0.5, preferably 0.001 to 0.4, more preferably from 0.001 to 0.3, most preferably from 0 to 0.2; q, r, s, and t represent the mole fraction of M, Si, Al, and P as tetrahedral oxides, where M is a metal selected from one of Group IA, IIA, IB, IIIB, IVB, VB, VIB, VIIB, VIIIB and Lanthanide's of the Periodic Table of Elements. Preferably M is selected from one of the group consisting of Co, Cr, Cu, Fe, Ga, Ge, Mg, Mn, Ni, Sn, Ti, Zn, and Zr. In an embodiment, p is greater than or equal to 0.2 and q, r, s, and t are greater than or equal to 0.001. In another embodiment, p is greater than 0.1 to about 1, q is greater than 0.001 to about 0.25, r is greater than 0.01 to about 0.15, s is in the range of from 0.4 to 0.5, and t is in the range of from 0.25 to 0.5. More preferably p is from 0.15 to 0.7, q is from 0.001 to 0.1, r is from 0.01 to 0.1, s is from 0.4 to 0.5, and t is from 0.3 to 0.5.

In another embodiment, the metalloaluminophosphate molecular sieve is a mixture of AEI and/or CHA framework type molecular sieves which has an AEI/CHA framework type ratio of from about 0/100 to about 40/60 as determined by DIFFaX analysis. In one embodiment, the metalloaluminophosphate molecular sieve is substantially free of non-CHA framework type molecular sieve. The term "substantially free", as used herein, means less than 5 wt. %, preferably less than 1 wt. %, even more preferably less than 0.5 wt. % of the metalloaluminophosphate molecular sieve having non-CHA framework type molecular sieve.

As used herein, the term "mixture" is synonymous with combination and is considered a composition of matter having two or more components in varying proportions, regardless of their physical state. In reference to molecular sieve structure, it encompasses physical mixtures, as well as intergrowths of at least two different molecular sieve structures; such as, for example those described in PCT Publication No. WO 98/15496 and co-pending U.S. Ser. No. 09/924,016, filed Aug. 7, 2001. In one embodiment, the molecular sieve is an intergrowth material having two or more distinct phases of crystalline structures within one molecular sieve composition. In another embodiment, the molecular sieve comprises at least one intergrown phase of AEI and CHA framework types. For example, SAPO-18, ALPO-18, and RUW-18 have an AEI framework-type, and SAPO-34 has a CHA framework-type. In a further embodiment the molecular sieve comprises a mixture of intergrown material, and non-intergrown material.

Intergrown molecular sieve phases are disordered planar intergrowths of molecular sieve frameworks. These are generally described in the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are periodically ordered in three dimensions. Structurally disordered structures show periodic ordering in dimensions less than three, i.e., in two, one, or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistic stacking sequences.

The molecular sieves of the present invention are disordered planar intergrowths of end-member structures AEI and CHA. We refer to A. Simmen et al. in Zeolites (1991), Vol. 11, pp. 654-661, describing the structure of molecular sieves with AEI and CHA framework types. For AEI and CHA, the Periodic Building Unit is a double six-ring layer. There are two types of layers "a" and "b", which are identical except "b" is the mirror image of "a" (180° rotation about the plane normal or mirror operation perpendicular to the plane normal). When layers of the same type stack on top of one another, i.e., aaa or bbb, the framework type CHA is generated. When layers "a" and "b" alternate, i.e., abab, the framework type AEI is generated. The molecular sieves of the present invention are made of stackings of layers "a" and "b" which contain regions of CHA framework type and regions of AEI framework type. Each change of CHA to AEI framework type is a stacking disorder or planar fault.

Preferably, the molecular sieves of the invention possess an AEI/CHA ratio of from about 7/93 to 38/62, more preferably from about 8/92 to 35/65, even more preferably from about 9/91 to 33/67, most preferably from about 10/90 to 30/70 as determined by DIFFaX analysis, using the powder X-ray diffraction (XRD) pattern of a calcined sample of the metalloaluminophosphate molecular sieve.

The X-ray diffraction data referred to herein are collected with a SCINTAG X2 X-Ray Powder Diffractometer (Scintag Inc., USA), using copper K-alpha radiation. The diffraction data are recorded by step-scanning at 0.02 degrees of two-theta (2θ), where theta is the Bragg angle, and a counting time of 1 second for each step. Prior to recording of each experimental X-ray diffraction pattern, the sample must be in the anhydrous state and free of any template used in its synthesis, since the simulated patterns are calculated using only framework atoms, not water or template.

While not wishing to be bound by theory, we believe that the combination of addition of metal, silicon source, and the preparation procedure contribute to a large extent to the small particle size, which is characterized by the FWHM and SEM.

Given the sensitivity of metalloaluminophosphate materials to water at recording temperatures, the molecular sieve samples are calcined after preparation and kept moisture-free according to the following procedure. About 2 grams of each molecular sieve sample are heated in an oven from room temperature under a flow of nitrogen at a rate of 3° C./minute to 200° C. and, while retaining the nitrogen flow, the sample is held at 200° C. for 30 minutes and the temperature of the oven is then raised at a rate of 2° C./minute to 650° C. The sample is then retained at 650° C. for 8 hours, the first 5 hours being under nitrogen and the final 3 hours being under air. The oven is then cooled to 200° C. at 30° C./minute and, when the XRD pattern is to be recorded, the sample is transferred from the oven directly to a sample holder and covered with Mylar foil to prevent rehydration. It is also possible after cool-down to room temperature, to do a fast recording of the XRD pattern immediately after removal of the Mylar foil (e.g., by using a total scan time of less than 5 minutes).

The full-width-half-maximum (FWHM) is measured by measuring the fill width at the half maximum intensity after background subtraction of any XRD peak in unit of degree (2θ). In one embodiment, the molecular sieve of this invention has an X-ray diffraction pattern having a FWHM greater than 0.1 degree (2θ), preferably greater than 0.15 degree (2θ), and, optionally, greater than 0.4 degree (2θ). In another embodiment, the molecular sieve of this invention has an X-ray diffraction pattern having a FWHM greater than 0.1 degree (2θ) for the peak at 20.6 degree (2θ), preferably greater than 0.15 degree (2θ) for the peak at 20.6 degree (2θ), and optionally greater than 0.4 degree (2θ) for the peak at 20.6 degree (2θ).

In the case of crystals with planar faults, interpretation of XRD diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A (1991), Vol. 433, pp. 499-520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA, SAV, and KFI, as reported by K. P. Lillerud et al. in "Studies in Surface Science and Catalysis", 1994, Vol. 84, pp. 543-550. DIFFaX is a well-known and established method to characterize crystalline materials with planar faults such as the intergrown molecular sieves of the present invention.

As the ratio of AEI increases relative to CHA in the intergrown phase, one can observe a decrease in intensity of certain peaks, for example, the peak at about 2θ=25.0 and an increase in intensity of other peaks, for example, the peak at about 2θ=17.05 and the shoulder at 2θ=21.2. Intergrown phases with AEI/CHA ratios of 50/50 and above (AEI/CHA≧1.0) show a broad feature centered at about 16.9 (2θ). Intergrown phases with AEI/CHA ratios of 40/60 and lower (AEI/CHA≦0.67) show a broad feature centered at about 18 (2θ).

Preferably, the molecular sieves obtained by the method of the present invention are relatively rich in CHA framework type. Such CHA-rich SAPOs are, for example, characterized by powder XRD diffraction patterns obtained from samples after calcination and avoiding re-hydration after calcination, having at least the reflections in the 5 to 25 (2θ) range as shown in Table 1 below.

TABLE 1

| 2θ (CuKα) |
|---|
| 9.3-9.6 |
| 12.7-13.0 |
| 13.8-14.0 |
| 15.9-16.1 |
| 17.7-18.1 |
| 18.9-19.1 |

TABLE 1-continued

| 2θ (CuKα) |
|---|
| 20.5-20.7 |
| 23.7-24.0 |

The XRD diffraction patterns of CHA-rich intergrown phases of AEI/CHA may also be characterized by the absence of peaks in the 9.8 to 12.0 (2θ) range and the absence of any broad feature centered at about 16.9 (2θ). A further characteristic is the presence of a peak in the 17.7 to 18.1 (2θ) range. The reflection peak in the 17.7-18.1 (2θ) range has a relative intensity between 0.09 and 0.4, preferably between 0.1 and 0.35 with respect to the reflection peak at 17.9 (2θ) in the diffraction pattern of SAPO-34, all diffraction patterns being normalized to the intensity value of the reflection peak in the 20.5-20.7 (2θ) range.

The metalloaluminophosphate molecular sieves made by the process of the present invention comprise at least one intergrown phase of molecular sieves having the AEI and CHA framework types. Preferably the CHA molecular sieve is SAPO-34 and the AEI molecular sieve is selected from SAPO-18, ALPO-18, or a mixture of SAPO-18 and ALPO-18. Also, the metalloaluminophosphates of the present invention advantageously have a silica to alumina molar ratio ($SiO_2/Al_2O_3$) ranging from 0.01 to 0.6, more preferably from 0.02 to 0.20, even more preferably from 0.03 to 0.19. Most preferred metalloaluminophosphate molecular sieves have a silica to alumina molar ratio from about 0.13 to about 0.24, for example, from about 0.15 to about 0.22, such as from about 0.17 to about 0.21, such as about 0.18 or about 0.19. The silica to alumina molar ratio ($SiO_2/Al_2O_3$) is preferably determined by chemical analysis.

The metalloaluminophosphate molecular sieves of this invention has a shredded crystal morphology by SEM. Shredded crystal morphology is as exemplified by FIG. 1.

The metalloaluminophosphate molecular sieves of this invention has at least 90 wt. % of the metalloaluminophosphate molecular sieve having a particle size less than 1 micron, preferably below 600 nm, more preferably less than 300 nm. and yet more preferably less than 100 nm, most preferably less than 50 nm.

In one embodiment, the molecular sieves of the present invention are prepared by a process that comprises:

(a) combining at least one silicon source, at least one metal source, at least one structure-directing-agent (R), at least one phosphorus source, at least one aluminum source to form a mixture having a molar composition according to formula (III):

$$(n)Si:Al_2:(m)P:(x)R:(y)H_2O:(z)M \quad (III)$$

wherein n is in the range of from about 0.005 to about 0.6, m is in the range of from about 1.2 to about 2.4, x is in the range of from about 0.5 to about 2, y is in the range of from about 10 to about 60, and z is in the range of from about 0.001 to 1; and (b) submitting the mixture to crystallization conditions to form the metalloaluminophosphate molecular sieve.

Preferably, n is in the range of from 0.005 to 0.5. In another preferred embodiment, n is in the range of from about 0.05 to about 0.4, such as from about 0.1 to about 0.3. Preferably, m is in the range of from 1.2 to 2.2. In another preferred embodiment, m is in the range of from about 1.2 to about 2, such as from about 1.5 to about 1.8. Preferably, x is in the range of from 0.5 to 1.5. In another preferred embodiment, x is in the range of from about 0.5 to about 1, such as from about 0.8 to about 0.9. Preferably, y is in the range of from 10 to 40. In another preferred embodiment, y is in the range of from about 10 to about 30, such as from about 10 to about 20. Preferably, z is in the range of from 0.01 to 0.9, more preferably z is in the range of from 0.02 to 0.9, and most preferably z is in the range of from 0.05 to 0.9. In another preferred embodiment, z is in the range of from about 0.1 to about 0.4, such as from about 0.1 to about 0.3.

In another embodiment, the molecular sieves of the present invention are prepared by a process that comprises:

(a) combining at least one silicon source, at least one metal source, at least one structure-directing-agent (R), at least one phosphorus source, at least one aluminum source to form a mixture having a molar composition according to formula (IV):

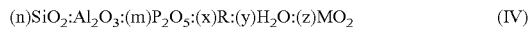

$$(n)SiO_2:Al_2O_3:(m)P_2O_5:(x)R:(y)H_2O:(z)MO_2 \qquad (IV)$$

wherein n is in the range of from about 0.005 to about 0.6, m is in the range of from about 0.6 to about 1.2, x is in the range of from about 0.5 to about 2, y is in the range of from about 10 to about 60, and z is in the range of from about 0.001 to 1; and (b) submitting the mixture to crystallization conditions to form the metalloaluminophosphate molecular sieve.

Preferably, n is in the range of from 0.005 to 0.5. In another preferred embodiment, n is in the range of from about 0.05 to about 0.4, such as from about 0.1 to about 0.3. Preferably, m is in the range of from 1.2 to 2.2. In another preferred embodiment, m is in the range of from about 1.2 to about 2, such as from about 1.5 to about 1.8. Preferably, x is in the range of from 0.5 to 1.5. In another preferred embodiment, x is in the range of from about 0.5 to about 1, such as from about 0.8 to about 0.9. Preferably, y is in the range of from 10 to 40. In another preferred embodiment, y is in the range of from about 10 to about 30, such as from about 10 to about 20. Preferably, z is in the range of from 0.01 to 0.9, more preferably z is in the range of from 0.02 to 0.9, and most preferably z is in the range of from 0.05 to 0.9. In another preferred embodiment, z is in the range of from about 0.1 to about 0.4, such as from about 0.1 to about 0.3.

It will be understood that the molar ratio of silica to alumina in the reaction mixture will influence the silica to alumina ratio of the molecular sieve after synthesis.

In one embodiment, the molecular sieves of the present invention have a composition represented by empirical formula (V) on an anhydrous basis as:

$$pR\bullet(M_qSi_rAl_sP_t)O_2 \qquad (V)$$

wherein p is in the range of from about 0.001 to about 0.5, preferably 0.001 to 0.4, more preferably from 0.001 to 0.3, most preferably from 0.001 to 0.2; q, r, s, and t represent the mole fraction of M, Si, Al, and P as tetrahedral oxides, where M is a metal selected from one of Group IA, IIA, IB, IIIB, IVB, VB, VIB, VIIB, VIIIB, and Lanthanide's of the Periodic Table of Elements, preferably M is selected from one of the group consisting of Co, Cr, Cu, Fe, Ga, Ge, Mg, Mn, Ni, Sn, Ti, Zn, and Zr. In an embodiment, p is greater than or equal to 0.2, and q, r, s, and t are greater than or equal to 0.01. In another embodiment, p is greater than 0.1 to about 1, q is greater than 0.001 to about 0.25, r is greater than 0.01 to about 0.15, s is in the range of from 0.4 to 0.5, and t is in the range of from 0.25 to 0.5, more preferably p is from 0.15 to 0.7, q is from 0.0001 to 0.1, r is from 0.01 to 0.1, s is from 0.4 to 0.5, and t is from 0.3 to 0.5.

Treatment of the synthesis mixture to form the desired crystalline molecular sieve typically takes place by hydrothermal treatment, and is preferably carried out under autogenous pressure, for example, in an autoclave, preferably a stainless steel autoclave, optionally, teflon lined. The treatment may, for example, be carried out at a temperature within the range of from 50° C., preferably from 90° C., especially 120° C. to 250° C. The treatment may, for example, be carried out for a period within the range of from 1 to 200 hours, preferably up to 100 hours, depending on the temperature. The procedure may include an aging period, either at room temperature or at a moderately elevated temperature, before the hydrothermal treatment at more elevated temperatures takes place. The latter may include a period of gradual or stepwise variation in temperature.

In a preferred embodiment, the metal used is Zn and/or Mg. These metals in the synthesis mixture are introduced as acetate, chloride, nitrate or sulfate salt, for example, zinc acetate, zinc nitrate, magnesium acetate, and magnesium nitrate.

In a preferred embodiment, the phosphorus used phosphoric acid. The phosphorus in the synthesis mixture is introduced as phosphoric acid, organic phosphates, e.g., triethylphosphate and aluminophosphates.

In a preferred embodiment, the aluminum used is alumina hydrate and/or alumina. The aluminum in the synthesis mixture is introduced as alumina hydrate, alumina, sodium aluminate, pseudoboehmite, organic aluminum sources, e.g., alkoxides, for example, aluminum isopropoxide and aluminum phosphate.

In a preferred embodiment, the silicon is fumed silica. The silicon in the synthesis mixture is introduced as fumed silica, e.g., that sold under the trade name Aerosil; an aqueous colloidal suspension of silica, e.g., that sold under the trade name Ludox AS40 or Ludox HS40; or organic silicon sources, e.g., a tetraalkyl orthosilicate, especially tetraethyl orthosilicate, although the invention is more especially of importance when the source of silicon is an inorganic source, it being understood that dissolution in the basic organic solvent may effect physical or chemical changes in the source as added.

In addition, the synthesis mixture will contain a structure-directing template (hereinafter "template"), preferably an organic structure-directing agent. In general, these compounds are organic bases, especially nitrogen-containing bases, more especially amines and quaternary ammonium compounds, used either singly or in mixtures.

The amount of organic structure-directing agent is such that the molar ratio of directing agent to alumina is less than 2, preferably from about 0.5 to about 2, preferably from about 0.6 to about 1.5, such as from about 0.7 to about 1.

While not wishing to be bound by theory, we believe that the addition of relatively small amount of a metal (represented by M) provides a very significant improvement in the yield of the molecular sieve. Accordingly, this invention uses low amounts of expensive structure-directing templates per unit alumina and surprisingly produces higher molecular sieve yields, as illustrated in the examples below. Compared to molecular sieve synthesis processes not employing the metal (M) that use higher template to alumina molar ratios, the present invention provides a synthesis method that is less expensive and that produces higher overall yields of molecular sieve. In one embodiment, this invention has a metalloaluminophosphate molecular sieve yield at least 0.5 wt. %, preferably 1 wt. %, higher than the yield obtained with a synthesis mixture having a template to alumina molar ratio of 1 or higher. As shown in the examples, it is possible to secure 10 wt. % or greater yield improvements through use of the present invention. However, it may often be desirable to use a smaller amount of the metal M than that necessary to secure the max yield improvement.

As structure-directing templates there may be mentioned, for example, tetraethyl ammonium compounds, cyclopentylamine, aminomethyl cyclohexane, piperidine, dimethyl cyclohexyl amine, triethylamine, cyclohexylamine, trimethyl hydroxyethylamine, morpholine, dipropylamine (DPA), pyridine, isopropylamine, and mixtures thereof. Preferred templates are triethylamine, cyclohexylamine, piperidine, pyridine, isopropylamine, tetraethyl ammonium compounds, dipropylamine, and mixtures thereof. The tetraethylammonium compounds include tetraethyl ammonium hydroxide (TEAOH), and tetraethyl ammonium phosphate, fluoride, bromide, chloride, and acetate. Preferred tetraethyl ammonium compounds are the hydroxide and the phosphate. The molecular sieve structure may be effectively controlled using combinations of templates.

Thermal treatment of the molecular sieve synthesis mixture may be carried out with or without agitation, such as stirring or tumbling (rotating the vessel about a "horizontal axis". If desired, the synthesis mixture may be stirred or tumbled during an initial part of the heating stage, for example, from room temperature to an elevated temperature, e.g., the final treatment temperature, and be static for the remainder of the thermo-treatment.

In one practical embodiment, the crystallization process of the invention comprises at least two stages; namely a first stage in which the (silico)aluminophosphate precursor material is produced and a second stage in which the precursor material is converted into the desired intergrown AEI/CHA framework type molecular sieve. In the first stage, the synthesis mixture is heated under agitation to raise its temperature at a rate of at least 8° C./hour to a first temperature of about 99° C. to about 150° C., such as about 115° C. to about 125° C. The synthesis mixture is then maintained at said first temperature, preferably with the agitation being continued, for a time, typically from about 0.5 hours to about 120 hours, to form an intermediate product mixture containing a slurry of the precursor material. The intermediate product mixture is then heated so as to raise its temperature at a rate of at least 8° C./hour, such as at a rate of from about 10° C./hour to about 40° C./hour, to a second temperature generally from about 150° C. to about 220° C., such as about 165° C. to about 190° C. This second heating step can be conducted under static conditions or with reduced agitation as compared with the first heating step. The second synthesis mixture is then maintained at said second temperature until the intergrown molecular sieve crystallizes from the mixture, which generally takes from about 2 to about 150 hours; such as from about 5 to about 100 hours, for example, from about 10 to about 50 hours.

The invention contemplates the use of a silicon source in the form of the silicon component in a solution, preferably a basic organic solution, in the hydrothermal synthesis of a metalloaluminophosphate molecular sieve to reduce the particle size of the product.

Typically, the molecular sieve product is formed as a slurry and can be recovered by standard means, such as by centrifugation or filtration. The separated molecular sieve product can also be washed, recovered by centrifugation or filtration and dried, or can be stored as an aqueous slurry.

As a result of the molecular sieve crystallization process, the recovered molecular sieve contains within its pores at least a portion of the template used. The crystalline structure essentially wraps around the template, and the template should be removed to obtain catalytic activity. In a preferred embodiment, activation is performed in such a manner that the template is removed from the molecular sieve, leaving active catalytic sites with the microporous channels of the molecular sieve open for contact with a feedstock. The activation process is typically accomplished by calcining, or essentially heating the molecular sieve comprising the template at a temperature of from 200 to 800° C. in the presence of an oxygen-containing gas. In some cases, it may be desirable to heat the molecular sieve in an environment having a low oxygen concentration. This type of process can be used for partial or complete removal of the template from the intracrystalline pore system. In other cases, particularly with smaller templates, complete or partial removal from the sieve can be accomplished by conventional desorption processes.

The metalloaluminophosphate catalyst may be pretreated under pre-treatment conditions sufficient to remove metal from framework. Inventors anticipate that the metal removed from framework may reside in the cage of the molecular sieve which may improve both catalytic activity and/or selectivity. While not wishing to be bound by theory, catalytic selectivity may be improved due to partial blockage of the cage by the metal removed from the framework. Also, the metal removed from framework metal may have higher activity than the metal incorporated by conventional method, such as, ion-exchange.

Once the molecular sieve is made, it can be formulated into a catalyst by combining the molecular sieve with other materials that provide additional hardness or catalytic activity to the finished catalyst product. When combined with these other materials, the resulting composition is typically referred to as a metalloaluminophosphate catalyst, with the catalyst comprising the molecular sieve. This invention also relates to catalysts comprising the molecular sieves of this invention.

Materials that can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica, or silica sol, and mixtures thereof. These components are also effective in reducing overall catalyst cost, acting as a thermal sink to assist in heat shielding the catalyst during regeneration, densifying the catalyst and increasing catalyst strength. When blended with non-metalloaluminophosphate molecular sieve materials, the amount of molecular sieve contained in the final catalyst product is in the range of from 10 to 90 wt. % of the total catalyst, preferably 20 to 70 wt. % of the total catalyst.

The metalloaluminophosphate molecular sieves synthesized in accordance with the present method can be used to dry gases and liquids; for selective molecular separation based on size and polar properties; as ion-exchangers; as catalysts in cracking, hydrocracking, disproportionation, alkylation, isomerization, and oxidation; as chemical carriers; in gas chromatography; and in the petroleum industry to remove normal paraffins from distillates.

The metalloaluminophosphate molecular sieves of the present invention are particularly suited for the catalytic conversion of oxygenates to hydrocarbons. Accordingly, the present invention also relates to a method for making an olefin product from an oxygenate feedstock wherein the oxygenate feedstock is contacted with the catalyst of this invention comprising the molecular sieve of this invention under conditions effective to convert the oxygenate feedstock to olefin products. When compared to other metalloaluminophosphates under the same operating conditions, the metalloaluminophosphates of the present invention exhibit higher selectivity to light olefins, and produce fewer by-products.

In this process a feedstock containing an oxygenate contacts a catalyst comprising the molecular sieve in a reaction zone of a reactor at conditions effective to produce light olefins, particularly ethylene and propylene. Typically, the oxygenate feedstock is contacted with the catalyst containing the molecular sieve when the oxygenate is in vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

In this oxygenate conversion process, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 525° C. is preferred.

In a preferred embodiment, it is highly desirable to operate at a temperature of at least 300° C. and a Temperature Corrected Normalized Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Preferred pressures are in the range of about 5 kpa-a to about 5 MPa-a, with the most preferred range being of from about 50 kPa-a to about 0.5 MPa-a. The foregoing pressures are exclusive of any oxygen depleted diluent, and thus, refer to the partial pressure of the oxygenates and/or mixtures thereof with feedstock.

The process can be carried out in a dynamic bed system or any system using a variety of transport beds, although a fixed-bed system could be used. It is particularly desirable to operate the reaction process at high space velocities.

The process may be carried out in a batch, semi-continuous, or continuous fashion. The process can be conducted in a single reaction zone or a number of reaction zones arranged in series or in parallel.

The conversion of oxygenates to produce olefins is preferably carried out in a large-scale continuous catalytic reactor. This type of reactor includes fluid-bed reactors and concurrent riser reactors as described in "Free Fall Reactor," *Fluidization Engineering*, D. Kunii and O. Levenspiel, Robert E. Krieger Publishing Co. NY, 1977, incorporated in its entirety herein by reference. Additionally, countercurrent free fall reactors may be used in the conversion process. See, for example, U.S. Pat. No. 4,068,136 and "Riser Reactor", *Fluidization and Fluid-Particle Systems*, pp. 48-59, F. A. Zenz and D. F. Othmo, Reinhold Publishing Corp., NY, 1960, the descriptions of which are expressly incorporated herein by reference.

Any standard commercial scale reactor system can be used, for example, fixed-bed or moving bed systems. The commercial scale reactor systems can be operated at a weight hourly space velocity (WHSV) of from 1 hr$^{-1}$ to 1000 hr$^{-1}$. In the case of commercial scale reactors, WHSV is defined as the weight of hydrocarbon in the feedstock per hour per weight of metalloaluminophosphate molecular sieve content of the catalyst. The hydrocarbon content is the oxygenate content and the content of any hydrocarbon which may be present with the oxygenate. The metalloaluminophosphate molecular sieve content means only the metalloaluminophosphate molecular sieve portion that is contained within the catalyst. This excludes components such as binders, diluents, inerts, rare earth components, etc.

One or more inert diluents may be present in the feedstock, for example, in an amount of from 1 to 95 mol. %, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof. The preferred diluents are water and nitrogen. Water can be injected in either liquid or vapor form.

The level of conversion of the oxygenates is maintained to reduce the level of unwanted by-products. Conversion is also maintained sufficiently high to avoid the need for commercially undesirable levels of recycling of unreacted feeds. A reduction in unwanted by-products is seen when conversion moves from 100 mol. % to about 98 mol. % or less. Recycling up to as much as about 50 mol. % of the feed is preferred. Therefore, conversions levels which achieve both goals are from about 50 mol. % to about 98 mol. % and, desirably, from about 85 mol. % to about 98 mol. %. However, it is also acceptable to achieve conversion between 98 mol. % and 100 mol. % in order to simplify the recycling process. Oxygenate conversion is maintained using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is used, the molecular sieve catalyst can be continuously introduced as a moving bed to a regeneration zone where it is regenerated, such as, for example, by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include, but are not necessarily limited to lower straight and branched chain aliphatic alcohols and their unsaturated counterparts. Examples of suitable oxygenates include, but are not limited to: methanol; ethanol; n-propanol; isopropanol;

$C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenates are methanol, dimethyl ether, or a mixture thereof. The most preferred oxygenate compound is methanol.

The process for making an olefin product from an oxygenate feedstock by contacting the oxygenate feedstock with a catalyst comprising a metalloaluminophosphate of the present invention has good catalytic performance. This is reflected by a selectivity to ethylene and propylene equal to or greater than 75.0%, and/or an ethylene to propylene ratio equal to or greater than 0.75 and/or a selectivity to propane equal to or lower than 1.0%.

The method of making the olefin products from an oxygenate feedstock can include the additional step of making the oxygenate feedstock from hydrocarbons such as oil, coal, tar sand, shale, biomass, and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming, and partial oxidation.

One skilled in the art will also appreciate that the olefin products made by the oxygenate-to-olefin conversion reaction using the molecular sieve of the present invention can be polymerized to form polyolefins, particularly polyethylenes and polypropylenes. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

In addition to polyolefins, numerous other olefin derivatives may be formed from the olefins recovered from this invention. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

Another particular use of the composite material of the invention is in the reaction of organic oxygenates with ammonia to produce monoalkylamines and dialkylamines, particularly methylamine and dimethylamine. Examples of suitable organic oxygenate compounds for use in this reaction include alcohols having 1 to 3 carbon atoms, specifically, methanol, ethanol, n-propanol and isopropanol, and their ether counterparts, including methyl ethyl ether, dimethyl ether, diethyl ether and di-isopropyl ether. The reaction is conducted, preferably, but not exclusively, in a flowing system in a gaseous fixed bed or fluidized bed, with the molar ratio of ammonia to oxygenate being generally from about 0.5 to about 20, such as about 1 to about 5. The reaction conditions typically include a temperature of about 200 to 400° C., such as about 250 to about 360° C., a pressure of about 0.1 to about 10 MPa, such as about 0.5 to about 2 MPa and gas hourly space velocity, GHSV, of about 100 to about 10,000 $hr^{-1}$.

EXAMPLES

The following Examples, in which parts are by weight unless otherwise indicated, illustrate preferred embodiments of the invention. The source and purity of starting materials are those first given, unless indicated otherwise.

Yield is calculated by dividing the weight of the product (washed and dried overnight at 120° C.) by the initial weight of the gel as following:

$$Yield = \frac{Product\ dry\ weight\ (g)}{Initial\ gel\ weight\ (g)}\%.$$

SEM was obtained on a JEOL JSM-6340F Field Emission Scanning Electron Microscope, using a magnification of 20,000 times at a voltage of 2 keV.

In these examples, the XRD diffraction patterns were recorded on a SCINTAG X2 X-Ray Powder Diffractometer (Scintag Inc. USA), using copper Kα radiation. The molecular sieve samples were calcined after preparation and kept moisture-free according to the following procedure:

About 2 grams of molecular sieve were heated-up from room temperature to 200° C. under a flow of nitrogen at a rate of 2° C. per minute. The temperature was held at 200° C. for 30 minutes. Then the sample was heated-up from 200° C. to 650° C. under nitrogen at a rate of 2° C. per minute. The sample was held at 650° C. under nitrogen for 5 hours. Nitrogen was then replaced by air and the sample was kept at 650° C. under air for 3 hours. The sample was then cooled to 200° C. and kept at 200° C. to prevent hydration. The hot sample was then transferred into the XRD sample cup and was covered by Mylar foil to prevent hydration. XRD diffraction patterns were recorded in the 2θ range of 12 to 24 degrees.

In these examples, DIFFaX analysis was used to determine the AEI/CHA ratio of the molecular sieves. For the purpose of this application, the DIFFaX analysis was performed as disclosed in U.S. Pat. No. 6,812,372, fully incorporated herein by reference. If the molecular sieve contained more than one AEI/CHA intergrown phase, DIFFaX analysis was performed as disclosed in U.S. patent application Ser. No. 11/072,830.

Comparative Example

A synthesis mixture with the following molar ratios (VI) was prepared with the quantities indicated in the table:

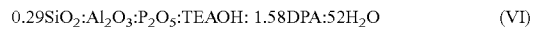

0.29$SiO_2$:$Al_2O_3$:$P_2O_5$:TEAOH: 1.58DPA:52$H_2O$ (VI)

by adding Ludox AS40 ($SiO_2$ 40 wt. % in water) to a mixture of phosphoric acid, water and Condea Pural SB ($Al_2O_3$ pseudoboehmite containing 25 wt. % of water). TEAOH (Eastern Chemical) was added to the mixture and followed by DPA (Eastern Chemical). The homogeneous slurry was heated in a stainless steel autoclave to 175° C. in 2 hours and kept at this temperature for 60 hrs. After cooling the product was washed and dried overnight at 120° C. The yield calculated by dividing the weight of the dried product by the initial weight of the gel was 11.1%. According to XRD, the product was having the CHA framework type structure with a particle size ranging between 0.5 and 20 microns as measured by SEM. The solid product has a Si/Al$_2$ ratio of 0.33 measured by chemical analysis.

Example 1

A synthesis mixture with the following molar ratios (VII) was prepared with the quantities indicated in Table 2:

$$0.05SiO_2:Al_2O_3:P_2O_5:TEAOH:35H_2O:0.025MgO \quad (VII)$$

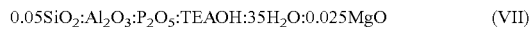

by adding Ludox AS40 (SiO$_2$ 40 wt. % in water) to a diluted solution of phosphoric acid and TEAOH (Eastern Chemical). The Magnesium acetate tetrahydrate (Fluka p.a. >99.5%) was added. The Condea Pural SB (Al$_2$O$_3$ pseudoboehmite containing 25 wt. % of water) was added to this mixture. The homogeneous slurry was heated in a stainless steel autoclave to 175° C. with a heating rate of 20° C./hr and kept at this temperature for 56 hrs. Tumbling (60 rpm) was applied during the whole hydrothermal treatment. After cooling the product was washed and dried overnight at 120° C. The yield calculated by dividing the weight of the dried product by the initial weight of the gel was 20.6%. According to XRD, the product was an intergrown phase of molecular sieves having AEI and CHA framework types, with a particle size of less than 0.5 micron as measured by SEM. The solid product has a AEI/CHA ratio of 20/80 as determined by DIFFaX. The solid product has a Si/Al$_2$ ratio of 0.06 and Mg/Al$_2$ ratio of 0.04 measured by chemical analysis. The FWHM of the XRD peak around 20.6 degree (2θ) is greater than 0.1 degree (2θ).

AEI and CHA framework types, with a particle size of less than 1.0 micron as measured by SEM. The solid product has a AEI/CHA ratio of 20/80 as determined by DIFFaX. The solid product has a Si/Al$_2$ ratio of 0.07 and Mg/Al$_2$ ratio of 0.03 measured by chemical analysis. The FWHM of the XRD peak around 20.6 degree (2θ) is greater than 0.1 degree (2θ).

Example 3

A synthesis mixture with the following molar ratios (IX) was prepared as described in Example 1 with the quantities indicated in Table 2:

$$0.05SiO_2:Al_2O_3:P_2O_5:TEAOH:35H_2O:0.1MgO \quad (IX)$$

The homogeneous slurry was heated in a stainless steel autoclave to 175° C. with a heating rate of 20° C./hr and kept at this temperature for 48 hrs. Tumbling (60 rpm) was applied during the whole hydrothermal treatment. After cooling the product was washed and dried overnight at 120° C. The yield calculated by dividing the weight of the dried product by the initial weight of the gel was 22.7%. According to XRD, the product has CHA framework type and is substantially free of non-CHA framework type molecular sieve, with a particle size of less than 0.3 micron as measured by SEM. The solid product has a Si/Al$_2$ ratio of 0.06 and Mg/Al$_2$ ratio of 0.12

TABLE 2

| Component | Proportion (Comparative Example) | Proportion (Example 1) | Proportion (Example 2) | Proportion (Example 3) | Proportion (Example 4) | Proportion (Example 5) |
|---|---|---|---|---|---|---|
| Colloidal silica (Ludox AS40) 40 wt. % in water | 22.5 | 0.89 | 0.98 | 0.99 | 1 | 1.8 |
| TEAOH, (Eastern Chemical) 35 wt. % in water | 183.31 | 51.19 | 51.11 | 50.94 | 50.4 | 50.7 |
| DPA (Dipropylamine, Eastern Chemical | 80.79 | 0 | 0 | 0 | 0 | 0 |
| MgAc$_2$, (Aldrich Co.), 99.5 wt. % | 0 | 0.66 | 1.3 | 2.6 | 5.12 | 5.15 |
| Al$_2$O$_3$ (Condea Pural SB) | 68.06 | 16.6 | 16.47 | 16.35 | 14.67 | 14.67 |
| H$_3$PO$_4$ (Acros), 85 wt. % in water | 115.74 | 28.21 | 28.06 | 27.86 | 27.86 | 27.58 |
| Water | 284.71 | 28.11 | 27.26 | 26.5 | 26.19 | 25.64 |
| Yield (%) | 11.1 | 20.6 | 21.8 | 22.7 | 24.3 | 25.2 |

Example 2

A synthesis mixture with the following molar ratios (VIII) was prepared as described in Example 1 with the quantities indicated in Table 2:

$$0.05SiO_2:Al_2O_3:P_2O_5:TEAOH:35H_2O:0.05MgO \quad (VIII)$$

The homogeneous slurry was heated in a stainless steel autoclave to 175° C. with a heating rate of 20° C./hr and kept at this temperature for 48 hrs. Tumbling (60 rpm) was applied during the whole hydrothermal treatment. After cooling the product was washed and dried overnight at 120° C. The yield calculated by dividing the weight of the dried product by the initial weight of the gel was 21.8%. According to XRD, the product was an intergrown phase of molecular sieves having measured by chemical analysis. The FWHM of the XRD peak around 20.6 degree (2θ) is greater than 0.1 degree (2θ).

Example 4

A synthesis mixture with the following molar ratios (X) was prepared as described in Example 1 with the quantities indicated in Table 2:

$$0.05SiO_2:0.9Al_2O_3:P_2O_5:TEAOH:35H_2O:0.2MgO \quad (X)$$

The homogeneous slurry was heated in a stainless steel autoclave to 175° C. with a heating rate of 20° C./hr and kept at this temperature for 48 hrs. Tumbling (60 rpm) was applied during the whole hydrothermal treatment. After cooling the product was washed and dried overnight at 120° C. The yield calculated by dividing the weight of the dried product by the initial weight of the gel was 24.3%. According to XRD, the product has CHA framework type and is substantially free of non-CHA framework type molecular sieve. The SEM shows fragmented particles. The solid product has a $Si/Al_2$ ratio of 0.06 and $Mg/Al_2$ ratio of 0.22 measured by chemical analysis. The FWHM of the XRD peak around 20.6 degree (2θ) is greater than 0.1 degree (2θ).

Example 5

A synthesis mixture with the following molar ratios (XI) was prepared as described in Example 1 with the quantities indicated in Table 2:

$$0.05SiO_2:0.9Al_2O_3:P_2O_5:TEAOH:35H_2O:0.02MgO \tag{XI}$$

The homogeneous slurry was heated in a stainless steel autoclave to 175° C. with a heating rate of 20° C./hr and kept at this temperature for 48 hrs. Tumbling (60 rpm) was applied during the whole hydrothermal treatment. After cooling the product was washed and dried overnight at 120° C. The yield calculated by dividing the weight of the dried product by the initial weight of the gel was 25.2%. According to XRD, the product was an intergrown phase of molecular sieves having AEI and CHA framework types. The SEM shows fragmented particles. The solid product has a AEI/CHA ratio of 10/90 as determined by DIFFaX. The solid product has a $Si/Al_2$ ratio of 0.10 and $Mg/Al_2$ ratio of 0.25 measured by chemical analysis. The FWHM of the XRD peak around 20.6 degree (2θ) is greater than 0.1 degree (2θ).

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A process for manufacturing a metalloaluminophosphate molecular sieve, said process comprising the steps of:
    (a) combining at least one silicon source, at least one metal source, at least one structure-directing-agent (R), at least one phosphorus source, and at least one aluminum source to form a mixture having a molar composition according to formula (XII):

$$(n)Si:Al_2:(m)P:(x)R:(y)H_2O:(z)M \tag{XII}$$

wherein n is in the range of from about 0.005 to about 0.6, m is in the range of from about 1.2 to about 2.4, x is in the range of from about 0.5 to about 2, y is in the range of from about 10 to about 60, and z is in the range of from about 0.001 to 1; and (b) submitting said mixture to crystallization conditions to form said metalloaluminophosphate molecular sieve, wherein said metalloaluminophosphate molecular sieve has an X-ray diffraction pattern having a FWHM greater than 0.10 degree (2θ) and an AEI/CHA framework type ratio of from about 0/100 to about 40/60 as determined by DIFFaX analysis.

2. The process of claim 1, wherein said step (b) further comprises an agitation step.

3. The process of claim 1, wherein said crystallization conditions comprise a temperature range between about 100° C. and about 250° C.

4. The process of claim 1, wherein said metal source comprises at least one of magnesium compounds, zinc compounds, or any combination thereof.

5. The process of claim 1, wherein said structure-directing-agent comprises at least one of tetraethylammonium hydroxide, tetraethylammonium phosphate, tetraethylammonium fluoride, tetraethylammonium bromide, tetraethylammonium chloride, tetraethylammonium acetate, cyclopentylamine, aminomethyl cyclohexane, piperidine, dimethyl cyclohexyl amine, triethylamine, cyclohexylamine, trimethyl hydroxyethylamine, morpholine, dipropylamine (DPA), pyridine, isopropylamine, or any combination thereof.

6. The process of claim 1, wherein said structure-directing-agent comprises tetraethylammonium hydroxide.

7. The process of claim 1, wherein said metalloaluminophosphate molecular sieve has a composition represented by empirical formula (XIII) on an anhydrous basis as:

$$pR\bullet(M_qSi_rAl_sP_t)O_2 \tag{XIII}$$

wherein p is in the range of from about 0.001 to about 0.5, q is in the range of from about 0.001 to about 0.25, r is in the range of from about 0.01 to about 0.15, s is in the range of from about 0.01 to about 0.6, t is in the range of from about 0.01 to 0.6, and the sum of q, r, s, and t is 1.

8. The process of claim 7, wherein said q is in the range of from about 0.01 to about 0.25.

9. The process of claim 7, wherein said metalloaluminophosphate molecular sieve has a shredded crystal morphology by SEM.

10. The process of claim 7, wherein, after calcination, said metalloaluminophosphate molecular sieve has an X-ray diffraction pattern having a FWHM greater than 0.15 degree (2θ).

11. The process of claim 1, wherein said silicon source comprises an inorganic silicon compound.

12. The process of claim 11, wherein said inorganic silicon compound is a colloidal silica.

13. The process of claim 1, wherein at least 90 wt. % of said metalloaluminophosphate molecular sieve has a particle size less than 100 nm.

14. The process of claim 1, wherein said metalloaluminophosphate molecular sieve is substantially free of non-CHA framework type.

15. The process of claim 14, wherein at least 90 wt. % of said metalloaluminophosphate molecular sieve has a particle size less than 100 nm.

16. The process of claim 14, wherein, after calcination, said metalloaluminophosphate molecular sieve has an X-ray diffraction pattern having a FWHM greater than 0.15 degree (2θ).

17. The process of claim 1, wherein said metalloaluminophosphate molecular sieve has an AEI/CHA ratio of from about 7/93 to 38/62.

18. The process of claim 17, wherein, after calcination, said metalloaluminophosphate molecular sieve has an X-ray diffraction pattern having at least one reflection peak in each of the following ranges in the 5 to 25 (2θ) range:

| 2θ (CuKα) |
| --- |
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0. |

19. The process of claim 18, wherein said X-ray diffraction pattern has no reflection peak in the 9.8 to 12.0 (2θ) range.

20. The process of claim 18, wherein said X-ray diffraction pattern has no broad feature centered at about 16.9 (2θ).

21. The process of claim 1, wherein said metalloaluminophosphate molecular sieve has a shredded crystal morphology by SEM.

22. The process of claim 1, wherein said metalloaluminophosphate molecular sieve has a silica to alumina molar ratio ($SiO_2/Al_2O_3$) ranging from 0.03 to 0.19.

23. A metalloaluminophosphate molecular sieve manufactured by a process comprising the steps of:
(a) combining at least one silicon source, at least one metal source, at least one structure-directing-agent (R), at least one phosphorus source, at least one aluminum source to form a mixture having a molar composition according to formula (XIV):

(n)Si:Al$_2$:(m)P:(x)R:(y)H$_2$O:(z)M     (XIV)

wherein n is in the range of from about 0.005 to about 0.6, m is in the range of from about 1.2 to about 2.4, x is in the range of from about 0.5 to about 2, y is in the range of from about 10 to about 60, and z is in the range of from about 0.001 to 1; and
(b) submitting said mixture to crystallization conditions to form said metalloaluminophosphate molecular sieve, wherein said metalloaluminophosphate molecular sieve has an X-ray diffraction pattern having a FWHM greater than 0.10 degree (2θ) and an AEI/CHA framework type ratio of from about 0/100 to about 40/60 as determined by DIFFaX analysis.

24. The metalloaluminophosphate molecular sieve of claim 23, wherein at least 90 wt. % said metalloaluminophosphate molecular sieve has a particle size less than 100 nm.

25. The metalloaluminophosphate molecular sieve of claim 23, wherein said step (b) further comprises an agitation step.

26. The metalloaluminophosphate molecular sieve of claim 23, wherein said crystallization conditions comprise a temperature range between about 100° C. and about 250° C.

27. The metalloaluminophosphate molecular sieve of claim 23, wherein said metal source comprises at least one of magnesium compounds, zinc compounds, or any combination thereof.

28. The metalloaluminophosphate molecular sieve of claim 23, wherein said structure-directing-agent comprises at least one tetraethylammonium hydroxide, tetraethylammonium phosphate, tetraethylammonium fluoride, tetraethylammonium bromide, tetraethylammonium chloride, tetraethylammonium acetate, cyclopentylamine, aminomethyl cyclohexane, piperidine, dimethyl cyclohexyl amine, triethylamine, cyclohexylamine, trimethyl hydroxyethylamine, morpholine, dipropylamine (DPA), pyridine, isopropylamine, or any combination thereof.

29. The metalloaluminophosphate molecular sieve of claim 23, wherein said structure-directing-agent comprises tetraethylammonium hydroxide.

30. The metalloaluminophosphate molecular sieve of claim 23 has a composition represented by empirical formula (XV) on an anhydrous basis as:

pR●(M$_q$Si$_r$Al$_s$P$_t$)O$_2$     (XV)

wherein p is in the range of from about 0.001 to about 0.5, q is in the range of from about 0.001 to about 0.25, r is in the range of from about 0.01 to about 0.15, s is in the range of from about 0.01 to about 0.6, t is in the range of from about 0.01 to 0.6, and the sum of q, r, s, and t is 1.

31. The metalloaluminophosphate molecular sieve of claim 30, after calcination, has an X-ray diffraction pattern having a FWHM greater than 0.15 degree (2θ).

32. The metalloaluminophosphate molecular sieve of claim 30 having a shredded crystal morphology by SEM.

33. The metalloaluminophosphate molecular sieve of claim 23, wherein said silicon source comprises an inorganic silicon compound.

34. The metalloaluminophosphate molecular sieve of claim 33, wherein said inorganic silicon compound is a colloidal silica.

35. The metalloaluminophosphate molecular sieve of claim 23, wherein said metalloaluminophosphate molecular sieve has substantially free of non-CHA framework type.

36. The metalloaluminophosphate molecular sieve of claim 35, wherein at least 90 wt. % said metalloaluminophosphate molecular sieve has a particle size less than 100 nm.

37. The metalloaluminophosphate molecular sieve of claim 23, wherein said metalloaluminophosphate molecular sieve has an AEI/CHA ratio of from about 7/93 to 38/62.

38. The metalloaluminophosphate molecular sieve of claim 37, after calcination, wherein said metalloaluminophosphate molecular sieve has an X-ray diffraction pattern having at least one reflection peak in each of the following ranges in the 5 to 25 (2θ) range:

| 2θ (CuKα) |
| --- |
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0. |

39. The metalloaluminophosphate molecular sieve of claim 38, wherein said X-ray diffraction pattern has no reflection peak in the 9.8 to 12.0 (2θ) range.

40. The metalloaluminophosphate molecular sieve of claim 38, wherein said X-ray diffraction pattern has no broad feature centered at about 16.9 (2θ).

41. The metalloaluminophosphate molecular sieve of claim 23, after calcination, wherein said metalloaluminophosphate molecular sieve has an X-ray diffraction pattern having a FWHM greater than 0.15 degree (2θ).

42. The metalloaluminophosphate molecular sieve of claim 23, wherein said metalloaluminophosphate molecular sieve has a silica to alumina molar ratio ($SiO_2/Al_2O_3$) ranging from 0.02 to 0.20.

43. A metalloaluminophosphate molecular sieve, said metalloaluminophosphate molecular sieve having a composition represented by empirical formula (XVI) on an anhydrous basis as:

$$pR\bullet(M_qSi_rAl_sP_t)O_2 \quad \text{(XVI)}$$

wherein p is in the range of from about 0.001 to about 0.5, q is in the range of from about 0.001 to about 0.25, r is in the range of from about 0.01 to about 0.15, s is in the range of from about 0.01 to about 0.6, t is in the range of from about 0.01 to 0.6, and the sum of q, x, y, and z is 1, wherein said metalloaluminophosphate molecular sieve has an X-ray diffraction pattern having a FWHM greater than 0.10 degree (2θ) and an AEI/CHA framework type ratio of from about 0/100 to about 40/60 as determined by DIFFaX analysis.

44. The metalloaluminophosphate molecular sieve of claim 43, wherein at least 90 wt. % said metalloaluminophosphate molecular sieve has a particle size less than 100 nm.

45. The metalloaluminophosphate molecular sieve of claim 43, after calcination, wherein said metalloaluminophosphate molecular sieve has an X-ray diffraction pattern having a FWHM greater than 0.15 degree (2θ).

46. The metalloaluminophosphate molecular sieve of claim 43, after calcination, wherein said metalloaluminophosphate molecular sieve has substantially free of non-CHA framework type.

47. The metalloaluminophosphate molecular sieve of claim 46, wherein at least 90 wt. % said metalloaluminophosphate molecular sieve has a particle size less than 100 nm.

48. The metalloaluminophosphate molecular sieve of claim 43, after calcination, wherein said metalloaluminophosphate molecular sieve has an AEI/CHA ratio of from about 7/93 to 38/62.

49. The metalloaluminophosphate molecular sieve of claim 48, wherein said metalloaluminophosphate molecular sieve has a shredded crystal morphology by SEM.

50. The metalloaluminophosphate molecular sieve of claim 48, after calcination, wherein said metalloaluminophosphate molecular sieve has an X-ray diffraction pattern having a FWHM greater than 0.15 degree (2θ).

51. The metalloaluminophosphate molecular sieve of claim 48, after calcination, wherein said metalloaluminophosphate molecular sieve has an X-ray diffraction pattern having at least one reflection peak in each of the following ranges in the 5 to 25 (2θ) range:

| 2θ (CuKα) |
|---|
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0. |

52. The metalloaluminophosphate molecular sieve of claim 51, wherein said X-ray diffraction pattern has no reflection peak in the 9.8 to 12.0 (2θ) range.

53. The metalloaluminophosphate molecular sieve of claim 51, wherein said X-ray diffraction pattern has no broad feature centered at about 16.9 (2θ).

54. The metalloaluminophosphate molecular sieve of claim 43, after calcination, wherein said metalloaluminophosphate molecular sieve has a silica to alumina molar ratio ($SiO_2/Al_2O_3$) ranging from 0.02 to 0.20.

55. A process for the conversion of an oxygenate to olefins, the process comprising the steps of:
(i) contacting the oxygenate under catalytic conversion conditions with the metalloaluminophosphate molecular sieve made by a process comprising the steps of:
(a) combining at least one silicon source, at least one metal source, at least one structure-directing-agent (R), at least one phosphorus source, at least one aluminum source to form a mixture having a molar composition according to formula (XVII):

$$(n)Si:Al_2:(m)P:(x)R:(z)M \quad \text{(XVII)}$$

wherein n is in the range of from about 0.005 to about 0.6, m is in the range of from about 1.2 to about 2.4, x is in the range of from about 0.5 to about 2, and z is in the range of from about 0.001 to 1; and
(b) submitting said mixture to crystallization conditions to form said metalloaluminophosphate molecular sieve,
wherein said metalloaluminophosphate molecular sieve has an X-ray diffraction pattern having a FWHM greater than 0.10 degree (2θ) and an AEI/CHA framework type ratio of from about 0/100 to about 40/60 as determined by DIFFaX analysis; and
(ii) withdrawing the olefins.

56. The process of claim 55, wherein said oxygenate comprises at least one of methanol, ethanol, n-propanol, isopropanol, $C_4$-$C_{20}$ alcohols, methyl ethyl ether, dimethyl ether, diethyl ether, di-isopropyl ether, formaldehyde, dimethyl carbonate, dimethyl ketone, acetic acid, or any combination thereof.

57. The process of claim 55, wherein said oxygenate is methanol.

58. A process for the conversion of an oxygenate to alkylamines, the process comprising the steps of:
(i) contacting the oxygenate with ammonia under catalytic conversion conditions with the metalloaluminophosphate molecular sieve made by a process comprising the steps of:
(a) combining at least one silicon source, at least one metal source, at least one structure-directing-agent (R), at least one phosphorus source, at least one aluminum source to form a mixture having a molar composition according to formula (XVIII):

$$(n)Si:Al_2:(m)P:(x)R:(z)M \quad \text{(XVIII)}$$

wherein n is in the range of from about 0.005 to about 0.6, m is in the range of from about 1.2 to about 2.4, x is in the range of from about 0.5 to about 2, and z is in the range of from about 0.001 to 1; and
(b) submitting said mixture to crystallization conditions to form said metalloaluminophosphate molecular sieve,
wherein said metalloaluminophosphate molecular sieve has an X-ray diffraction pattern having a FWHM greater than 0.10 degree (2θ) and an AEI/CHA framework type ratio of from about 0/100 to about 40/60 as determined by DIFFaX analysis; and
(ii) withdrawing the alkylamines.

59. The process of claim 58, wherein said oxygenate is methanol.

* * * * *